United States Patent

Massardo et al.

[11] Patent Number: 4,594,451
[45] Date of Patent: Jun. 10, 1986

[54] BENZOYL-UREAS EXERTING AN INSECTICIDE ACTIVITY

[75] Inventors: Pietro Massardo, Milan; Franco Bettarini; Gabriele Giovarruscio, both of Novara; Paolo Piccardi; Franca Reggiori, both of Milan; Vincenzo Caprioli, San Martino; Angelo Longoni, Milan, all of Italy

[73] Assignee: Montedison S.p.A., Milan, Italy

[21] Appl. No.: 601,968

[22] Filed: Apr. 19, 1984

[30] Foreign Application Priority Data

Apr. 22, 1983 [IT] Italy ............................. 20744 A/83

[51] Int. Cl.[4] .......................................... C07C 127/22
[52] U.S. Cl. ........................................................ 564/44
[58] Field of Search .................................... 564/44, 23

[56] References Cited

U.S. PATENT DOCUMENTS 4,162,330 7/1979 Ehrenfreund .................... 564/44
4,414,211 11/1983 Rasmussen ..................... 260/245.5

FOREIGN PATENT DOCUMENTS 3217619 11/1983 Fed. Rep. of Germany ........ 564/44
2106499 4/1983 United Kingdom .................. 564/44

*Primary Examiner*—Charles F. Warren
*Assistant Examiner*—R. A. Picard

[57] ABSTRACT

There are described compounds of formula:

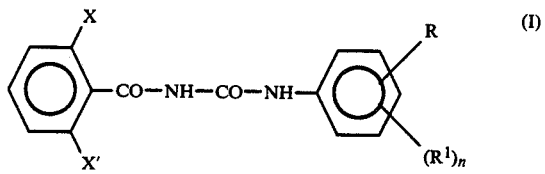

in which
X (or X')=H, F, Cl and X' (or X)=F, Cl;

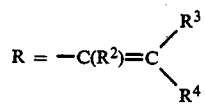

with $R^2$=H, Cl, Br, F an optionally halogen-substituted alkyl $C_1$–$C_3$;
$R^3$=halogen, an optionally halogen-substituted alkyl $C_1$–$C_3$;
$R^4$=H or $R^3$;
$R^1$=H, halogen, an optionally halogen-substituted alkyl $C_1$–$C_3$, $OCH_3$, $SCH_3$, $OCF_3$;
n=an integer from 1 to 4.

The compounds of formula I are endowed with a high insecticide activity which is mainly exerted against insects' larvae and eggs.

7 Claims, No Drawings

BENZOYL-UREAS EXERTING AN INSECTICIDE ACTIVITY

This invention relates to benzoyl-urea derivatives endowed with an insecticide activity and, more particularly, to 1-benzoyl-3-aryl-urea derivatives which are particularly active against eggs and larvae of insects which are harmful in the agrarian and civil fields, as well as to the use thereof.

The invention also relates to a process for synthetizing said benzoyl-ureas. Various derivatives of 1-benzoyl-3-aryl-urea endowed with insecticide activity are already known.

Among these derivatives, the first product in commerce is Difluorobenzuron, a trade designation for the compound 1-(2,6-difluorobenzoyl)-3-(4-chlorophenyl)-urea described in U.S. Pat. No. 3,993,908 (U.S. Phillips Corporation).

Difluorobenzuron, however, since it contains the unit of 4-chloro-aniline in its molecule, is suspected of being cancerogenic [European Chem. News 6 (16), 29 (1978)].

Among the various derivatives of 1-benzoyl-3-aryl-urea having an insecticide activity and described in literature, there may be cited the benzoyl-phenyl-ureas substituted in the phenyl radical by an ethynyl, which are described in European patent application No. 38766 (Ciba Geigy).

THE PRESENT INVENTION

We have now found new derivatives of 1-benzoyl-3-aryl-urea—which are the object of the present invention—having the general formula:

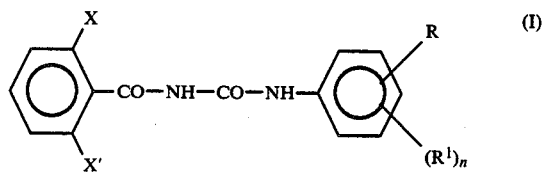 (I)

in which:
one out of X and X' is a hydrogen atom, a fluorine atom or a chlorine atom and the other is an atom of fluorine or of chlorine;
R represents a group

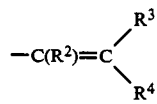

in which $R^2$ is an atom of hydrogen, of chlorine, of fluorine or of bromine, or an alkyl $C_1$–$C_3$ optionally substituted by 1 to 3 halogen atoms;
$R^3$ is a halogen atom or an alkyl $C_1$–$C_3$ optionally substituted by 1 to 3 halogen atoms;
$R^4$ is the same as $R^3$ or is a hydrogen atom;
$R^1$ represents a hydrogen atom, a halogen, an alkyl $C_1$–$C_3$ optionally substituted by 1 to 3 halogen atoms, a group $OCH_3$, $SCH_3$ or $OCF_3$;
n is an integer from 1 to 4.

The term "halogen" as used hereinabove, preferably means an atom of fluorine, chlorine or bromine.

The compounds of formula I are endowed with an insecticide activity and are suited to be employed in the agrarian forestal, domestic and veterinary fields, in the fight against infestations caused by insects.

In the description of the preparation of the compounds of formula I reported hereinbelow, the symbols X, X', R, $R^1$, $R^2$, $R^3$, $R^4$ and n have the meanings reported in formula I, unless otherwise specified.

The compounds of formula I are obtained by reacting a benzoyl-isocyanate of formula:

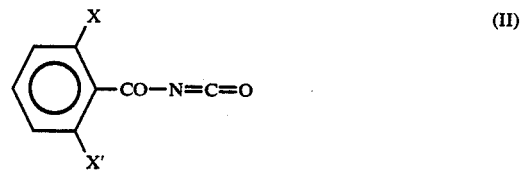 (II)

with an aromatic amine of formula:

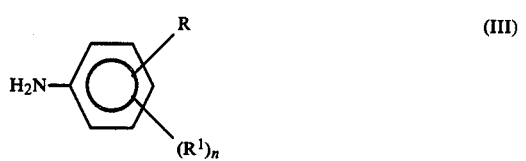 (III)

The reaction does not require the presence of catalysts and is carried out in an inert solvent and at a temperature ranging from 0° C. to the boiling temperature of the mixture.

Suitable solvents are aromatic hydrocarbons, chlorinated hydrocarbons, ethers, ketones and acetonitrile.

The benzoyl-isocyanates of formula II are known compounds, in some cases available in commerce.

The amines of formula III are new compounds and, as such, constitute a further object of the invention.

They are prepared by reduction, according to known techniques (for example with sodium sulphite or chlorinated tin), of the nitro-derivatives of formula:

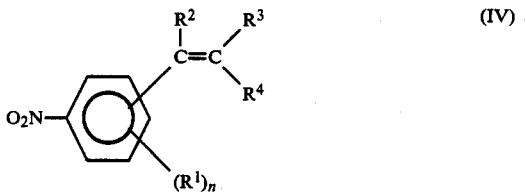 (IV)

The nitro-derivatives of formula IV can be prepared according to one of the following processes:

(a) starting from aromatic aldehydes or ketones of formula:

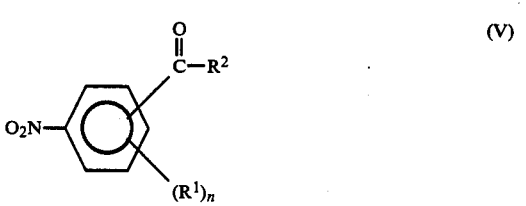 (V)

in which $R^2$=H (aldehyde) or alkyl (ketone).

The compounds of formula V are condensed in the presence of triphenyl-phosphine with a halogen-alkane of formula:

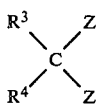

in which Z represents an atom of chlorine or bromine.

Examples of compounds of formula VI are $CCl_4$, $CBr_4$, $CH_3-CCl_3$, $CF_3-CBr_3$, $CF_3-CCl_3$ and $CF_3-CFBr_2$. The above reaction develops with the following stoichiometry (reaction 1):

$$(V)+(VI)+2P(C_6H_5)_3 \to (IV)+(C_6H_5)_3PO+(C_6H_5)_3PZ_2. \quad (1)$$

Reaction 1 is carried out in an inert solvent, such as e.g. a chlorinated hydrocarbon or dimethylformamide, at a temperature ranging from 0° C. to the boiling temperature of the mixture, optionally in the presence of stoichiometric amounts of powdered zinc. The reaction temperature and the use of powdered zinc substantially depend on the reactivity of the halogen-alkane of formula VI.

(b) Starting from aromatic aldehydes or ketones of formula:

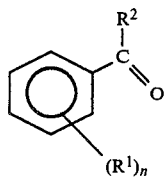

wherein $R^1$, $R^2$ and n have the above-reported meanings. Product VII is reacted with product VI, according to reaction 1, to obtain a vinyl-aromatic compound of formula:

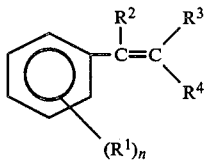

which is nitrated to obtain the nitro-derivatives of formula (IV) according to the following reaction 2:

$$VIII+NHNO_3 \to IV. \quad (2)$$

(c) Starting from aromatic nitro-bromide or aromatic nitro-iodide derivatives of formula:

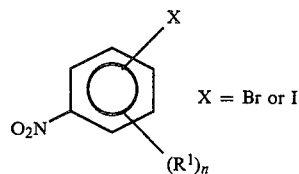

and coupling these derivatives with a halogenated olefin, according to the following reaction 3:

$$IX + CH_2=CH-C_{F3} \xrightarrow{Pd} IV \quad (3)$$

Reaction 3 is carried out in the presence of an inert solvent, such as dimethylformamide, and of a basic compound.

(d) Starting from an aryl-metal of formula:

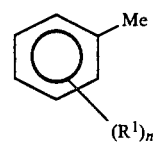

$Me = Li, Mg, X$, wherein
$X = Br$ or $I$
which is reacted with a halogenated olefin according to the following reaction 4:

$$XI+F_2C=CF-CF_3 \to VIII. \quad (4)$$

Reaction 4 is carried out in an inert anhydrous solvent, such as ether. Product VIII is nitrated according to reaction 2.

Reaction 1 is particularly suited to the preparation of the nitroderivatives of formula IV in which $R^3$ and $R^4$ represent a halogen atom or a halogen-substituted methyl. For preparing the compounds of formula IV, in which both $R^3$ and $R^4$ represent alkyl groups optionally halogen-substituted or in which $R^4$ is a hydrogen atom, it may be advisable to react the aldehyde or ketone of formula V with a Wittig reagent of formula:

$(Z=Cl, Br)$.

The nitroderivatives of formula IV, in which $R^2$ is an atom of chlorine or of bromine, can be prepared by halogenation (chlorination or bromination) and dehydrohalogenation of the compounds of formula IV in which $R^2$ is a hydrogen atom.

As is apparent to those skilled in the art, different alternative procedures for the synthesis of the intermediates and of the products of formula I are possible.

The amines of formula III, for example, do not necessarily require the reduction of a nitroderivative. They are obtainable according to a plurality of methods described in literature, see for example Saul Patai "The Chemistry of the Amino Group" Interscience Publishers N.Y. 1968.

An alternative procedure for the synthesis of the compound of formula I consists, for example, in reacting a benzamide of formula:

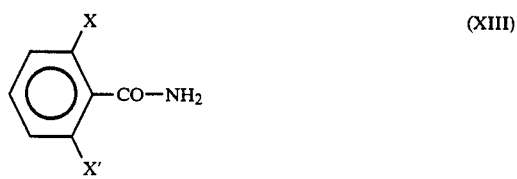

with an isocyanate of formula:

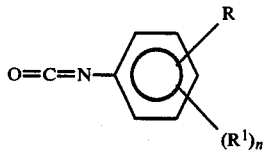

(XIV)

This reaction is carried out in conditions analogous with those described hereinbefore for the reaction between the benzoyl-isocyanate of formula II and the amine of formula III.

However, the preparation of the isocyanates of formula XIV envisages the preparation of the amines of formula III and the reaction thereof with phosgene.

This aspect, combined with the fact that the benzoyl-isocyanates of formula II are as available as the amides of formula XIII, generally leads to prefer the synthesis method indicated hereinbefore, namely the reaction between the compounds of formulas II and III.

As mentioned hereinabove, the compounds of formula I are endowed with a high insecticide activity which is mainly exerted against insects' larvae and eggs.

Among the insects, those which are particularly controllable with the compounds of formula I are the ones belonging to the orders of Diptera, Lepidoptera and Coleoptera.

These orders include several species which are important due to their harmfulness in the agrarian forestal, domestic and veterinary fields. Therefore, the compounds of formula I are suitable for various utilizations such as, for example, the defence of the agricultural cultivations from the infestations caused by phytophagous insects, the protection of the ambients infested by flies and mosquitos, the protection of the breeding animals from some parasites of the cattle, etc.

The compounds of formula I exhibit furthermore a collateral acaricide activity.

For the practical uses, the compounds of general formula I may be employed as such or, more properly, in the form of compositions containing, besides one or more of the compounds of formula I as an active principle, also solid or liquid inert vehicles and optionally other additives. According to the usual formulative practice, the compositions may be in the form of wettable powders, emulsifiable concentrates, etc.

The amount of active substance in the compositions varies over a wide range (1–95% by weight) depending on the type of composition and on the use it is intended for.

If particular situations do so require, or in order to extend the range of action, it is possible to add to the compositions other active substances, such as e.g. other insecticides or acaricides.

The amount of active substance (compound of formula I) to be distributed for the insecticide treatments depends on various factors such as, for example, the infestation type and degree, the substrate on which the infestation is present (agrarian cultivations, stretches of water and waterways, organic substrates of various nature) the type of composition utilized, climatic and environmental factors, available applicative means, etc. Generally, active substance amounts ranging from 0.01 to 1 kg/ha are sufficient for a good disinfestation.

The following examples are given to better illustrate the present invention.

In the nuclear magnetic resonance spectra ($^1$H-NMR) reported in the examples, the following abbreviations are used:

s = singlet
m = multiplet or unresolved complex signal
b (broad) = broadened signal
ABq = quartette of type AB.

EXAMPLE 1

Preparation of 4-(2,2-dibromovinyl)-nitrobenzene

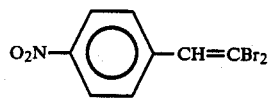

A solution of 5 g (0.0331 moles) of 4-nitro-benzaldehyde and 17 g (0.0662 moles) of triphenyl-phosphine in 50 ml of anhydrous $CH_2Cl_2$ was cooled to $-5°$–$0°$ C. and kept under stirring.

A solution of 12 g (0.036 moles) of $CBr_4$ in 20 ml of anhydrous $CH_2Cl_2$, was dropwise added to the above solution, in order that the temperature should not exceed 5° C.

After a few minutes, the formation of a precipitate was observed.

On completion of the addition, it was allowed to spontaneously heat to room temperature and the whole was maintained under stirring for further 30 minutes.

The reaction mixture was then filtered and the solvent was removed from the filtrate by evaporation under reduced pressure. The residue was then taken up in petroleum ether (200 ml in several portions). The solvent was then removed by evaporation under reduced pressure and the residue was purified by chromatography on a silica gel column (eluent: n.hexane-ethyl ether in the ratio of 9:1).

3.5 g of a product were obtained, having the above reported formula and the following nuclear magnetic resonance spectra:

$^1$H-NMR (CDCl$_3$, TMS): δ(ppm) 7.45 (s, 1H, CH=CBr$_2$). 7.85 (ABq, 4H, aromatic protons).

EXAMPLE 2

Preparation of 4-(2-bromo-3,3,3-trifluoro-1-propenyl)nitrobenzene

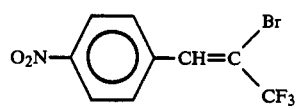

The product was prepared from 4-nitro-benzaldehyde and from 1,1,1-trifluoro-tribromoethane (CF$_3$—CBr$_3$) by operating according to the process of example 1. The obtained product has:

$^1$H-NMR (CDCl$_3$, TMS): δ(ppm) 7.7 (s, 1H,

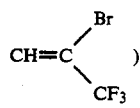
)

8.05 (Abq, 4H, aromatic protons).

EXAMPLE 3

Preparation of 4-(2-chloro-3,3,3-trifluoro-1-propenyl)nitrobenzene

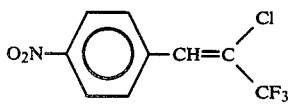

3.8 g of zinc in powder were added, in small portions, to a mixture, maintained under stirring and in a nitrogen atmosphere, consisting of 9 g of 4-nitro-benzaldehyde, 11 g of $CF_3$—$CCl_3$, 27.75 g of triphenyl-phosphine and 50 ml of dimethylformamide.

The reaction was exothermic and was controlled at 70° C. for 5 hours.

It was then poured into acidulated water (250 ml) and it was extracted with ethyl ether (2×125). The ether extract was anhydrified on anhydrous $Na_2SO_4$ and, after filtration, the solvent was removed by evaporation under reduced pressure. The rough product was subjected to chromatography on a silica gel column (eluent: n.hexane-ethyl ether in the ratio of 9:1). 4.5 g of the above product was so obtained, having:

$^1$H-NMR (CDCl$_3$, TMS): δ(ppm) 7.35 (s, 1H,

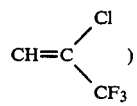

)

8.05 (ABq, 4H, aromatic protons).

EXAMPLE 4

Preparation of 3-chloro-4-(1,2,3,3,3 pentafluoro-1-propenyl)-nitrobenzene

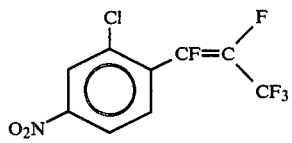

In a nitrogen atmosphere and under stirring, 2-lithiumchlorobenzene was prepared by reacting 42.2 ml (1.42M) of butyl-lithium, in 200 ml of anhydrous ether at −100° C., with 11.58 g of bromo-chloro-benzene in 50 ml of anhydrous ether. After 50 min. at −100° C., 9 g of exafluoro-propene was added by bubbling. The mixture was maintained at −95° C. for 3 h and then 10 ml of hydrochloric acid (37%) was added. The mixture was allowed to heat to room temperature, and after the phases separation, was neutralized and anhydrified on anhydrous $Na_2SO_4$. The solvent was removed by evaporation under reduced pressure and the residue was distilled at 41°-47° C./1 mm Hg. 5 g of the obtained 2-chloro (1,2,3,3,3-pentafluoro-1-propenyl)benzene was dropwise added, under stirring, to a mixture of 9.3 ml of $HNO_3$ (65%) and 5 ml of $H_2SO_4$ (96%), at 0° C.

The reaction was continued for 48 h at 20° C. and then the reaction mixture was poured into ice and extracted with ethyl ether (3×100).

The ether extract was neutralized and anhydrified. After concentration, 6 g of a raw product was obtained, which was purified by chromatography on silica gel column (eluent: hexane 95%—ethyl-acetate 5%). The obtained product has:

$^1$H-NMR (CDCl$_3$-TMS): δ(ppm) 7.35 (d, 1H, aromatic proton). 7.9 (d, 1H, aromatic proton). 8 (s, 1H, aromatic proton).

EXAMPLE 5

Preparation of 3-chloro-(2-chloro-3,3,3-trifluoro-1-propenyl)-nitrobenzene

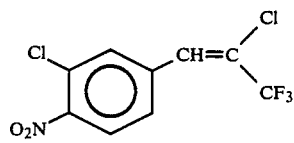

20 g of chloro-benzaldehyde were reacted, under stirring and in a nitrogen atmosphere, with 12 g of Zn in powder form and 37.5 g of triphenylphosphine in 150 ml of dimethylformamide.

26.8 g of $CH_3$—$CCl_3$ was dropwise added and the mixture was maintained for 3 h at 40° C. The reaction mixture was cooled, poured into water and extracted with ethyl-ether (3×100). The organic extract was concentrated and taken up with hexane.

The triphenylphosphine was removed by filtration and the organic residue was concentrated and distilled at 75° C./0.5 mm Hg.

11 g of the obtained 3-chloro-(2-chloro-3,3,3-trifluoro-1-propenyl)benzene was added dropwise, at 10° C. and under stirring, to a mixture of 15 ml of $H_2SO_4$ (96%) and 15 ml of $HNO_3$ (65%). The reaction was continued at 20° C. for 14 h and then the reaction mixture was poured into ice, neutralized and extracted with ethyl ether (3×100). 9 g of a raw product was obtained which is purified by chromatography on silica gel column (eluent:hexane 95%—ethyl ether 5%).

The obtained product has:

$^1$H-NMR (CDCl$_3$-TMS): δ(ppm) 7.3 (1H, s,

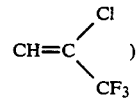

)

7.6–8.1 (m, 3H, aromatic protons).

EXAMPLE 6

Preparation of 3-chloro-4-(3,3,3 trifluoro-1-propenyl)nitro-benzene

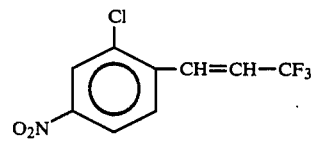

2.85 g of 3-chloro-4-iodo-nitro-benzene, 0.95 g of sodium acetate, 0.0048 g of Pd(OAc)$_2$, 0.048 g of triphenylphosphine and 2 g of 3,3,3-trifluoro-propene were reacted in 25 ml of dimethylformamide at 130° C. for 24 h, under stirring. The reaction mixture was cooled, breathered to atmospheric pressure, poured in water and extracted with ethyl ether (5×80 ml). The organic extract was anhydrified on $Na_2SO_4$ and purified by chromatography on silica gel column (hexane 95%—ethyl-acetate 5%).

1 g of product having the above reported formula was obtained, having

¹H-NMR (CDCl₃, TMS): δ(ppm): 5.95 (dq, 1H, =CH—CF₃). 7.1 (d, 1H, CH=CH—CF₃). 7.2–7.8 (m, 3H aromatic protons).

EXAMPLE 7

Preparation of 4-(2,2-dibromovinyl)-aniline

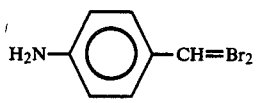

There was prepared a solution of 3.5 g of 4-(2,2-dibromovinyl)-nitrobenzene in the minimum methanol amount sufficient to dissolve all the product (about 40 ml). 30 ml of concentrated hydrochloric acid and 9 g SnCl₂ were added to the solution.

The reaction was exothermic and the whole was kept at 65° C. for 1 hour. 120 ml of aqueous NaOH at 10% were then gradually added and it was extracted with CH₂Cl₂ (2×100 ml).

The combined extracts were anhydrified and the solvent was removed by evaporation under reduced pressure. 2.6 g of the desired product were thus obtained.

¹H-NMR (CDCl₃, TMS): δ(ppm) 3.4 (b, 2H, NH₂). 6.95 (ABq, 4H, aromatic protons). 7.3 (s, 1H, CH=CBr₂).

EXAMPLE 8

By operating in like manner as is described in example 7, the nitro-derivatives of examples 2 to 6 were hydrogenated to the corresponding anilines:

4-(2-bromo-3,3,3-trifluoro-1-propenyl)-aniline

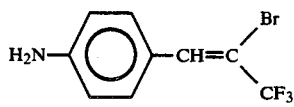

¹H-NMR (CDCl₃, TMS) δ(ppm) 3.9 (b, 2H, NH₂). 7.1 (ABq, 4H, aromatic protons). 7.4 (s, 1H,

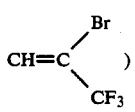

4-(2-chloro-3,3,3-trifluoro-1-propenyl)-aniline

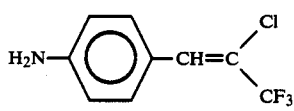

¹H-NMR (CDCl₃, TMS) δ(ppm) 3.7 (b, 2H, NH₂). 7.15 (s, 1H,

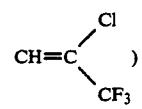

7.2 (ABq, 4H, aromatic protons).
2-chloro-4-(2-chloro-3,3,3-trifluoro-1-propenyl)-aniline

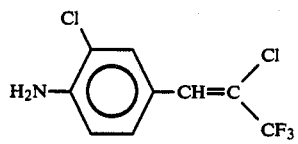

¹H-NMR (CDCl₃, TMS): 3.6 (b, 2H, NH₂). 7.05 (b, 3H, aromatic protons). 7.1 (s, 1H,

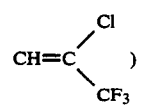

3-chloro-4-(3,3,3-trifluoro-1-propenyl)-aniline

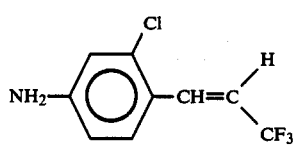

¹H-NMR (CDCl₃, TMS): 3.5 (b, 2H, NH₂). 5.5 (dq, 1H, =CH—CF₃). 6.9 (d, 1H, CH=CHCF₃). 7 (m, 3H, aromatic protons).
3-chloro-4-(1,2,3,3,3-pentafluoro-1-propenyl)-aniline

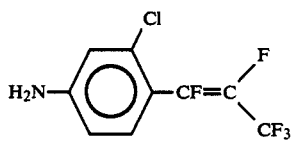

¹H-NMR (CDCl₃, TMS): 3.6 (b, 2H, NH₂). 7.05 (m, 3H, aromatic proton).

EXAMPLE 9

Preparation of 1-(2-chloro-benzoyl)-3-[4-(2,2-dibromovinyl)-phenyl]-urea (Compound No. 1)

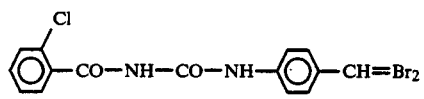

A solution of 2.6 g of 4-(2,2-dibromovinyl)-aniline and 1.3 g of (2-chloro-benzoyl)-isocyanate in 30 ml of ethyl ether was left under stirring at room temperature for 30 minutes.

A precipitate was formed, which was collected by filtration and recrystallized from acetone.

3.3 g of the desired product (a solid having a melting point of 190° C.) were so obtained.

¹H-NMR (CD₃COCD₃): δ(ppm) 7.4–7.9 (m, 9H). 10.6 (s, 1H, NH). 11.3 (s, 1H, NH).

EXAMPLE 10

Starting from (2-chlorobenzoyl)-isocyanate and from the first two anilines described in example 8, and operating under conditions analogous with the ones described in example 9, the following compounds were prepared:

1-(2-chloro-benzoyl)-3-[4-(2-bromo-3,3,3,-trifluoro-1-1-propenyl-phenyl]-urea (Compound No. 2)

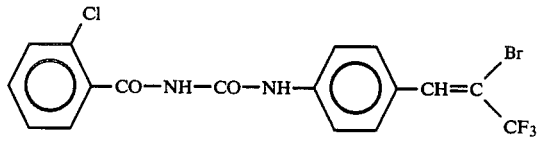

(melting point=185° C.)

1-(2-chloro-benzoyl)-3-[4-(2-chloro-3,3,3-trifluoro-1-1propenyl)-phenyl]-urea (Compound No. 3)

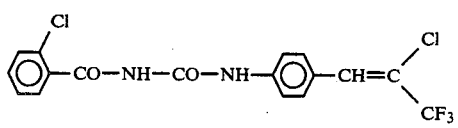

(melting point=205° C.)

EXAMPLE 11

Operating according to the process conditions of example 9, the following compounds were produced:

| Compound No. | | Melting Point |
|---|---|---|
| 4 | N—(2,6-dichloro-benzoyl)-N'—[4-(2-chloro-3,3,3-trifluoro-1-propenyl)-phenyl]urea | 210° C. |
| 5 | N—(2-chloro-benzoyl)-N'—[3-(2-bromo-3,3,3-trifluoro-1-propenyl)-phenyl]urea | 117° C. |
| 6 | N—(2,6-di-chloro-benzoyl)-N'—[3-(2-bromo-3,3,3-trifluoro-1-propenyl)-phenyl]urea | 174° C. |
| 7 | N—(2-chloro-benzoyl)-N'—[3-(2-chloro-3,3,3-trifluoro-1-propeny)-phenyl]urea | 106° C. |
| 8 | N—(2,6-di-chloro-benzoyl)-N'—[3-(2-chloro-3,3,3-trifluoro-1-propenyl)-phenyl]urea | 167° C. |
| 9 | N—(2-chlorobenzoyl)-N'—[4-(1-methyl-2,2-difluoro-vinyl)-phenyl]urea | 186° C. |
| 10 | N—(2-chlorobenzoyl)-N'—[4-(2,2-dichlorovinyl)-phenyl]urea | 193° C. |
| 11 | N—(2-chlorobenzoyl)-N'—[3-methoxy-4-(1,2,3,3,3-pentafluoro-1-propenyl)phenyl]urea | 149° C. |
| 12 | N—(2-chlorobenzoyl)-N'—[2-methoxy-3-(1,2,3,3,3-pentafluoro-1-propenyl)-phenyl]urea | 147° C. |
| 13 | N—(2-chlorobenzoyl)-N'—[3-methyl-4-(1,2,3,3,3-pentafluoro-1-propenyl)-phenyl]urea | 164° C. |
| 14 | N—(2-chlorobenzoyl)-N'—[2-methyl-3-(1,2,3,3,3-pentafluoro-1-propenyl)-phenyl]urea | 150° C. |
| 15 | N—(2,6-difluorobenzoyl)-N'—[4-(2-chloro-3,3,3-trifluoro-1-propenyl)-phenyl]urea | 223° C. |
| 16 | N—(2-chlorobenzoyl)-N'—[4-(3-methyl-1-propenyl)-phenyl]urea | 142° C. |
| 17 | N—(2-chlorobenzoyl)-N'—[4-chloro-3-(2-chloro-3,3,3-trifluoro-1-propenyl)-phenyl]urea | 139° C. |
| 18 | N—(2-chlorobenzoyl)-N'—[4-(3-chloro-1,1,1,4,4,4-exafluorobut-2-en-2-yl)-phenyl]urea | 212° C. |
| 19 | N—(2-chlorobenzoyl)-N'—[2-(3-chloro-1,1,1,4,4,4-exafluorobut-2-en-2-yl)-phenyl]urea | 134° C. |
| 20 | N—(2-chlorobenzoyl)-N'—[4-(1-trifluoromethyl-2,2-di-chloro-vinyl)-phenyl]urea | 204° C. |
| 21 | N—(2-chlorobenzoyl)-N'—[2-chloro-4-(2-chloro-3,3,3-trifluoro-1-propenyl)-phenyl]urea | 174° C. |
| 22 | N—(2-chlorobenzoyl)-N'—[4-(2-trifluoromethyl-1-propenyl)-phenyl]urea | 206° C. |
| 23 | N—(2-chlorobenzoyl)-N'—[4-(1-trifluoromethyl-2,2-difluoro-vinyl)-phenyl]urea | 168° C. |
| 24 | N—(2-chlorobenzoyl)-N'—[4-(2,3,3,3-tetrafluoro-1-propenyl)phenyl]urea | 183° C. |
| 25 | N—(2-chlorobenzoyl)-N'—[4-(3,3,3-trifluoro-1-propenyl)phenyl]urea | 191° C. |
| 26 | N—(2-chlorobenzoyl)-N'—[3-chloro-4-(3,3,3-trifluoro-1-propenyl)-phenyl]urea | 184° C. |
| 27 | N—(2-chlorobenzoyl)-N'—[4-(1-bromo-3,3,3-trifluoro-1-propenyl)-phenyl]urea | 177° C. |
| 28 | N—(2-chlorobenzoyl)-N'—[2-(2-chloro-3,3,3-trifluoro-1-propenyl)-4-chloro-phenyl]urea | 178° C. |
| 29 | N—(2-chlorobenzoyl)-N'—[3-methyl-(2-chloro-3,3,3-trifluoro-1-propenyl)-phenyl]urea | 143° C. |
| 30 | N—(2-chlorobenzoyl)-N'—[2-methoxy-3-(2-chloro-3,3,3-trifluoro-1-propenyl-phenyl]urea | 148° C. |
| 31 | N—(2-chlorobenzoyl)-N'—[4-methoxy-3-(2-chloro-3,3,3-trifluoro-1-propenyl)-phenyl]urea | 155° C. |
| 32 | N—(2-chlorobenzoyl)-N'—[3-methoxy-4-(2-chloro-3,3,3-trifluoro-1-propenyl)-phenyl]urea | 162° C. |
| 33 | N—(2-chlorobenzoyl)-N'—[2-(2-chloro-3,3,3-trifluoro-1-propenyl)-phenyl]urea | 142° C. |
| 34 | N—(2-chlorobenzoyl)-N'—[3-chloro-4-(1,2,3,3,3-pentafluoro-1-propenyl)-phenyl]urea | 161–162° C. |

EXAMPLE 12

Determination of the insecticide activity

Test 1

Immediate residual activity on larvae of *Spondoptera littoralis* (Lepidoptera).

Tobacco leaves were treated by mechanical spraying with a hydroacetonic solution of the product being tested at 10% by volume of acetone and containing a surfactant. After complete evaporation of the solvents, the leaves were infested with second-age larvae of the Lepidopter. The infested leaves were preserved in a suitably conditioned room for the entire duration of the test. In like manner, tobacco leaves treated only with a hydroacetonic solution at 10% of acetone and with the surfactant were infested and preserved, in order to be used as a check.

Ten days after the infestation and after having renewed the treated substrate at least one time, the dead larvae were counted with respect to the check.

Test 2

Activity on larvae of *Aedes aegypti* (Diptera)

Spring water (297 ml) was mixed with an acetonic solution (3 ml) of the product being tested, in a suitable concentration.

Into the resulting solution there were introduced 25 4-day old Dipter Larvae, which were properly fed.

As a check, other larvae were introduced into a hydroacetonic solution (3 ml of acetone, 297 ml of spring water) free from any active substance.

The number of dead larvae and pupae and of adults normally emerged from the cocoon was noted every 2–3 days, until conclusion of the insects' emergence from the cocoon in the check.

The activity of the product being tested is expressed as a percent ratio of dead individuals in respect of the total number of treated individuals.

The insecticide activity in the tests cited hereinbefore is expressed according to the following scale of values.
5 = complete activity (98–100%) of mortality)
4 = high activity (80–97%) of mortality
3 = fairly good activity (60–79% of mortality)
2 = sufficient activity (40–59% of mortality)
1 = poor activity (20–39% of mortality)
0 = negligible activity or no activity (0–19% of mortality).

The data relating to the insecticide activity at the indicated doses, expressed according to the scale of values reported hereinabove, are recorded on the following Table 1.

TABLE 1

| Compound No. | Insecticide activity Test 1 | | Test 2 |
| --- | --- | --- | --- |
| | dose: 0.001% | dose: 0.0005% | dose: 0.01 ppm |
| Check (*) | 1 | 0 | 1 |
| 1 | 5 | 5 | — |
| 2 | 5 | 5 | — |
| 3 | 5 | 5 | 5 |
| 4 | 5 | 5 | 5 |
| 5 | 5 | 4 | 0 |
| 6 | 5 | 4 | 0 |
| 7 | 4 | 3 | 2 |
| 8 | 5 | 3 | 2 |
| 9 | 4 | 3 | 4 |
| 10 | 2 | 1 | 1 |
| 11 | 2 | 1 | 0 |
| 12 | 2 | 1 | 1 |
| 13 | 2 | 1 | 0 |
| 14 | 4 | 3 | 1 |
| 15 | 5 | 5 | 5 |
| 16 | 3 | 2 | 2 |
| 17 | 5 | 5 | 0 |
| 18 | 2 | 1 | 0 |
| 19 | 2 | 1 | 0 |
| 20 | 2 | 1 | 0 |
| 21 | 5 | 4 | 4 |
| 22 | 5 | 5 | 0 |
| 23 | 4 | 3 | 0 |
| 24 | 5 | 5 | 0 |
| 25 | 5 | 5 | 0 |
| 26 | 5 | 5 | 5 |
| 27 | 5 | 4 | 4 |
| 28 | 3 | 2 | 0 |
| 29 | 5 | 4 | 4 |
| 30 | 3 | 2 | 0 |
| 31 | 2 | 1 | 0 |
| 32 | 2 | 1 | 0 |
| 33 | 3 | 2 | 0 |

TABLE 1-continued

| Compound No. | Insecticide activity Test 1 | | Test 2 |
| --- | --- | --- | --- |
| | dose: 0.001% | dose: 0.0005% | dose: 0.01 ppm |
| 34 | 5 | 4 | 0 |

(*) As a check there was used the compound 1-(2-chloro-benzoyl)-3-(4-ethynylphenyl)-urea of formula:

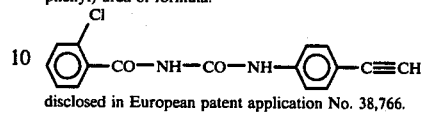

disclosed in European patent application No. 38,766.

What we claim is:

1. A compound formula:

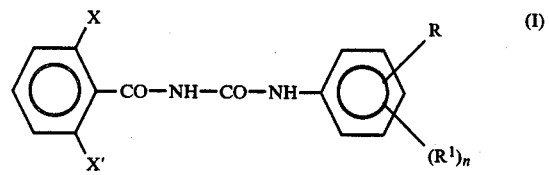

in which
one of X and X' is hydrogen, fluorine or chlorine and the other fluorine or chlorine;
R represents a group

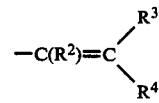

in which $R^2$ represents hydrogen, chlorine, fluorine, bromine or an alkyl $C_1$–$C_3$ optionally substituted by 1 to 3 halogen atoms;
$R^3$ represents a halogen atom or an alkyl $C_1$–$C_3$ optionally substituted by from 1 to 3 halogen atoms;
$R^4$ is the same as $R^3$ or represents a hydrogen atom;
$R^1$ represents a hydrogen atom, a halogen, an alkyl $C_1$–$C_3$ optionally substituted by from 1 to 3 halogen atoms, a group $OCH_3$, $SCH_3$ or $OCF_3$;
n is an integer from 1 to 4.

2. A compound according to claim 1, in which $R^1$ is a hydrogen atom.

3. A compound according to claim 1, in which substituent R is in position 4 with respect to the amino group.

4. A compound according to claim 1, and which is 1-(2-chlorobenzoyl)-3-[4-(2,2-dibromovinyl-phenyl]-urea.

5. A compound according to claim 1, and which is 1-(2-chloro-benzoyl)-3-[4-(2-bromo-3,3,3-trifluoro-1-propenyl)-phenyl]-urea.

6. A compound according to claim 1, and which is 1-(2-chloro-benzoyl)-3-[4-(2-chloro-3,3,3-trifluoro-1-propenyl)-phenyl]-urea.

7. Insecticide compositions containing, as an active ingredient, one or more of the compounds according to claim 1, solid or liquid inert vehicles and, optionally, other additives normally used in such compositions.

* * * * *